(12) United States Patent
Wang et al.

(10) Patent No.: US 10,308,616 B2
(45) Date of Patent: Jun. 4, 2019

(54) TRIFLUOROACETYL HYDRAZIDE COMPOUNDS AND METHODS OF PREPARATION AND USES THEREOF

(71) Applicant: GUANGZHOU MAGPIE PHARMACEUTICALS CO., LTD., Guangzhou (CN)

(72) Inventors: Yuqiang Wang, Guangzhou (CN); Haiyun Chen, Guangzhou (CN); Zaijun Zhang, Guangzhou (CN); Gaoxiao Zhang, Guangzhou (CN); Pei Yu, Guangzhou (CN); Yewei Sun, Guangzhou (CN); Luchen Shan, Guangzhou (CN); Liang Tao, Guangzhou (CN)

(*) Notice: Subject to any disclaimer, the term of this patent is extended or adjusted under 35 U.S.C. 154(b) by 26 days.

(21) Appl. No.: 15/731,538

(22) PCT Filed: Aug. 11, 2015

(86) PCT No.: PCT/CN2015/000581
§ 371 (c)(1),
(2) Date: Jun. 22, 2017

(87) PCT Pub. No.: WO2016/106760
PCT Pub. Date: Jul. 7, 2016

(65) Prior Publication Data
US 2018/0346430 A1 Dec. 6, 2018

(30) Foreign Application Priority Data
Dec. 31, 2014 (CN) .......................... 2014 1 0855931

(51) Int. Cl.
| C07D 241/12 | (2006.01) |
| A61K 31/4965 | (2006.01) |
| C07C 241/00 | (2006.01) |
| A61P 25/00 | (2006.01) |
| A61P 25/28 | (2006.01) |

(52) U.S. Cl.
CPC ........ *C07D 241/12* (2013.01); *A61K 31/4965* (2013.01); *A61P 25/00* (2018.01); *A61P 25/28* (2018.01); *C07C 241/00* (2013.01)

(58) Field of Classification Search
None
See application file for complete search history.

(56) References Cited

PUBLICATIONS

Chen et al., J. Mol. Neurosci. (2015) 56: 977-987.*
"Alzheimer's disease." CNN Health, Obtained Oct. 9, 2010, URL:http://www.cnn.com/2003/HEALTH/conditions/09/24/alzheimers.drug.ap/index.html.*
Antonio R. Damasio, Alzheimer's Disease and Related Dementias, Cecil Textbook of Medicine, 20th edition (1996), vol. 2, pp. 1992-1996.*

* cited by examiner

*Primary Examiner* — Alicia L Otton
(74) *Attorney, Agent, or Firm* — Panterrain IP Law; Charles Liu

(57) ABSTRACT

The present invention relates to trifluoroacetyl hydrazide compounds and methods of preparation and uses thereof. The compounds have a structure of the following formula:

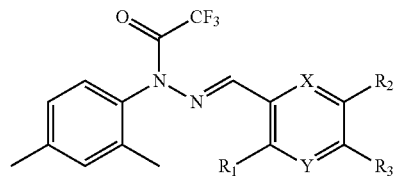

The compounds showed multifunctional mechanisms, including inhibition of glutamate excitotoxicity, activation of MEF2 transcriptional activity, clearance of free radicals, and promotion of nerve differentiation, and has a better protective effect on cells especially nerve cells. The compound can be used to prepare prophylactic or therapeutic medicaments with cytoprotective effects, for the prevention or treatment of diseases related to glutamate receptor activation, MEF2 disorders or excessive free radicals generation. The diseases include, for example, neurodegenerative diseases such as Alzheimer's disease, Parkinson and stroke, and the free radicals related diseases such as heart disease, myocardial ischemia, diabetes and other cardiovascular and cerebrovascular diseases.

4 Claims, 11 Drawing Sheets

Tetramethyl Pyrazine (TMP)

(E)-N-(2,4-Dimethylphenyl)-2,2,2-N'-(3,5,6-trimethyl pyrazine)-2-formaldehyde) trifluoroacetyl hydrazide (T-006)

Reagents and conditions: (a) $H_2O_2$, AcOH, 70 °C, 8 h; (b) $Ac_2O$, 125 °C, 3 h; (c) NaOH, rt. 5h; (d) $MnO_2$, EtOH, reflux, 3h; (e) dry EtOH, $N_2$, 10 min; (f) $Et_3N$, $(CF_3CO)_2O$, dry EtOH, $N_2$, 0 °C, 30 min.

TRIFLUOROACETYL HYDRAZIDE COMPOUNDS AND METHODS OF PREPARATION AND USES THEREOF

FIELD OF THE INVENTION

The present invention relates generally to the field of medicine and, more particularly, to multifunctional compounds with neuro-protective effects, and further particularly to trifluoroacetyl hydrazide compounds, methods of preparation and uses thereof for the prevention and treatment of diseases.

BACKGROUND OF THE INVENTION

Alzheimer's disease (AD) refers to a nervous system degenerative disease that severely affects the quality of life of the elderly. AD is the main type of senile dementia and the main cause of cognitive deterioration. According to multiple results of epidemiological surveys in China, the prevalence rate of AD in people over age 65 is about 5%, and its incidence increases with age generally. At present, there is no any drug that can be used to reverse cognitive impairment effectively. Acetylcholinesterase inhibitors (donepezil, rivastigmine, huperzine A, galanthamine) have some therapeutic effect on the patients with mild to moderate AD, but they may only temporarily alleviate symptoms and are not able to prevent further neuronal attenuation and also have some severe side effects. The combined application of cerebral blood flow and cerebral metabolism modifiers, such as oxiracetam, have shown to be effective in improving memory, but more often they are used as an intelligent improving reagent. The development of drugs related to amyloid precursor protein and amyloid β-protein seemed to be a promising approach until the release of clinical trial results for a series of secretase inhibitors provided by some major pharmaceutical companies such as Eli Lilly, and thus such approach may not be continued.

As AD may have different causes, the drug administration of single route or with single target may not be desirable; for the treatment of such disease, "one drug one target" is not an effective approach. A multifunctional drug refers to a drug having multiple treatment mechanisms for the same disease. Such multifunctional drugs are considered to have more potential than commonly used "one drug one target" drugs. Multifunctional drugs may be used for treating diseases such as cognitive and movement disorders, depression, schizophrenia, and other complicated diseases (Morphy et al. Drug Discov Today. 2004, 9(15): 641-651).

In the past, we made certain structural modifications over compound J147 synthesized by Professor Schubert of the Salk Institute, and also introduced a Ligustrazine moiety from traditional Chinese medicines to obtain compound T-006 with multifunctional therapeutic mechanisms. T-006 is a trifluoroacetyl hydrazide compound as used for the treatment of AD may have multiple mechanisms, including inhibiting glutamate receptor, activating MEF2 transcriptional activity, improving cognitive ability, neural differentiating, free radical scavenging, and protecting cells such as especially nerve cells.

Glutamate receptors may be divided into two types: the first type is ionic receptor, including N-methyl-D-aspartate receptor (NMDAR), kinase receptor (KAR) and α-amino-3-hydroxy-5-methyl-4-isoxazole receptor (AMPAR), which are coupled with ion channels to form receptor-channel compounds to mediate fast signal transduction; and the other type is of metabotropic receptors (mGluRs), which are coupled to G-proteins within the membrane. These receptors are activated to produce a slower physiological response through a signal transduction system consisting of G-protein effectors, second messengers, etc. (Wang S J, Yang T T, et al. Drug News Perspect, 2005, 18 (9): 561-566). Glutamate is the most abundant and important amino acid in the central nervous system for participating synaptic transmission and maintaining normal physiological functions of nerve cells. Under normal circumstances, the release, intake and re-absorption of glutamates remain in a dynamic equilibrium. However, if over release occurs or uptake is interrupted, glutamate may be accumulated in the brain which may cause a sharp increase in its concentration, while over activation of the receptor may cause a wide range of pathological damage on brain tissues (Kumar A, Zou L, Yuan X, et al. Journal of neuroscience research, 2002, 67(6): 781-786). Such excitotoxic effect of glutamate is closely related to the occurrence and development of various neurodegenerative diseases, and is shown as one of the important mechanisms leading to neuronal death in neurodegenerative diseases.

MEF2 includes four different isoforms (MEF2A-D) and is one of the first nuclear transcription factors found in muscle. It binds to the sequence of A/T enriched in DNA and regulates the expression of many genes involved in the formation and development of muscle. Many studies confirmed that MEF2 is not only highly expressed in muscle tissue, but also be abundant in the nervous system, and plays a regulating role in cell differentiation, growth, morphology, survival and apoptosis (Potthoff M J, Olson E N, et al. 134 (23): 4131-4140, McKinsey T A, Zhang C L, Olson E N, et al. Trends Biochem Sci, 2002, 27: 40-47). Many experiments show that MEF2 can regulate the growth of dependent synapsis and the formation of long-term memory, but the role of MEF2 in promoting memory formation is different from that of the traditional transcription factor CREB (Josselyn S A, Nguyen P V, et al. Curr Drug Targets CNS Neurol Disord, 2005, 4 (5): 481-497). The activation or inhibition of MEF2 is mainly determined by its DNA-binding affinity: PKA, CKII and GSK3β, p38, ERK5 and CaMKIV, PP2B may activate transcriptional activity of MEF2 through acetylation or ubiquitination of the C-terminal residues of MEF-2; whereas inhibition of transcriptional activity of MEF2 may be through binding to HSc70 of MEF2D through lysosomal degradation of neurotoxic substances and the expression of caspase; HDAC can inhibit the transcriptional activity of MEF2 through activation or inhibition by PP1α and CaMKIIα respectively (Rashid A J, Cole C J, et al. Genes, Brain and Behavior, 2014, 13 (1): 118-125). The expression of MEF2 can improve the survival rate of newborn neurons, while the mutation of MEF2C can lead to the increase of the number of apoptotic neurons and the loss of memory, which may cause a series of neurological diseases Wang et al. demonstrated that microtubule-associated protein Tau, involved in the pathogenesis of AD, is one of the substrates of glycogen kinase 3 (GSK3), and GSK3 inhibits the activity of MEF2D by direct phosphorylation, which process is involved in the degenerative changes of AD (Wang X, She H, et al. Journal of Biological Chemistry, 2009, 284(47): 32619-32626). The latest study by Professor Lipton indicates that the pathogenesis of PD is also associated with the inhibition of transcription between MEF2C-PGC1, which caused mitochondrial dysfunction, apoptosis and cell death (Ryan S D, Lipton S A, et al. Cell, 2013, 155 (6): 1351-1364).

One of the major pathological features of AD patients is amyloid beta deposition, commonly known as senile plaques. An important change of their behavior is learning and memory dysfunction. β-amyloid protein, abbreviated as Aβ, is produced by a series of secretase hydrolysis of its precursor protein APP. There are two main forms of Aβ; Aβ40 and Aβ42, wherein Aβ12 is of about 10%. Because of its high hydrophobicity, Aβ12 is easy to form fiber which is the major component of brain plaques (commonly known as senile plaques) found in the brains of patients with AD. Studies have indicated that a single Aβ does not produce toxic effects on the body, but the formation, aggregation and deposition of a large number of Aβ can cause a series of neurotoxicity, such as, interfering with synaptic activity, leading to protein dysfunction; inducing calcium influx leading to promote the phosphorylation of Tau protein, and the like (LaFerla F M, et al. Nature Reviews Neuroscience, 2007, 8(7): 499-509).

Oxidative stress refers to the physiological process of oxygen and antioxidant system imbalance caused by the body produces a large number of oxide intermediates when the body is stimulated. The imbalance tends to the generation of large amounts of free radicals and the activity of the antioxidant system is reduced, leading to oxidative damage to the body. These free radicals include reactive oxygen species (ROS) and reactive nitrogen species (RNS). The generation of free radicals is very complex and closely related to various physiological and biochemical processes (Conrad et al. Neurochem Int. 2013, 62(5):738-49). Because of the large number of polyunsaturated fatty acids in the phospholipid bilayers of neurons, which prone to lipid peroxidation, neuronal cells are more sensitive to oxidative stress than other cells (Facecchia K, et al. Journal of toxicology, 2011, 2011.). Oxygen metabolism damage in the central nervous system can produce more severe oxidative stress, leading to further damage to the nervous system (Mohsenzadegan et al. Iran J Allergy Asthma Immunol. 2012 September; 11 (3): 203-16). In the normal physiological condition, excessive free radicals and hydrogen peroxide (H2O2), singlet oxygen, ozone (O3) and other reactive oxygen species can be quickly cleared by the antioxidant system, but under the pathological conditions, this ability to remove is damaged. The accumulation of reactive oxygen species can cause nucleic acid fragmentation, enzyme passivation, polysaccharide depolymerization, and lipid peroxidation, eventually leading to neuronal death (Yan et al. Free Radic Biol Med. 2013; 62: 90-101). There are many factors that cause oxidative stress, and Aβ, metal ions, and mitochondria are all considered to play an important role in the process of oxidative stress. The content of soluble Aβ has a good linear relationship with the production rate of hydrogen peroxide. Aβ can change the permeability of calcium channels, activate NADPH oxidase II (NOX2), transfer electrons from NADPH to oxygen, increase the rate of ROS production, while Aβ has a strong affinity for metal ions with redox activity (Pimentel et al. Oxid Med Cell Longev. 2012; 2012:132-146). Aβ can produce hydrogen peroxide after binding to these active metal ions. Studies have shown that pro-oxidants can promote the production of Aβ, however antioxidants, such as vitamin E and other free radical scavengers can prevent Aβ damage to neurons and improve cognitive impairment.

Mitochondria are the main sites and the main donor of energy in the intracellular redox reaction, which produces more than 90% of the total free radicals in the cell. Thus, the normal function of the mitochondria has significance meaning for maintaining the normal physiological activity of the neurons (Yan et al. Free Radic Biol Med. 2013, 62:90-101). It has been suggested that various neurodegenerative diseases include Alzheimer's disease (AD), Parkinson's disease (PD), Huntington's disease (HD), amyotrophic lateral sclerosis (ALS) and progressive supranuclear palsy (PSP) and so on, mainly due to functional abnormality of neuronal mitochondria (Du et al. Int J Biochem Cell Biol. 2010, 42(5): 560-572). Quantitative morphological counts of different types of mitochondria (normal, partial damage, and complete damage) in the brain neurons of AD patients showed that the normal mitochondrial content of the AD neurons was significantly reduced and the content of completely damaged mitochondria was significantly increased, compared with the neurons in normal brain of the same age (Beal et al. Curr Opin Neurobiol. 1996 6(5): 661-6666). Mitochondrial damage leading to neuronal oxidative damage plays a major role in two aspects: one is to make the electron transport chain (ETC) dysfunction, so that free radical content increased, and the other is to reduce activity of mitochondrial antioxidant system by reducing content of mitochondrial glutathione, coenzyme Q, vitamin C, vitamin E and other antioxidant small molecules and some oxidation reaction catalytic enzymes.

The Salk Institute has completed major preclinical studies of pharmacology and toxicology of J147, and the preliminary test results if which fully demonstrated that trifluoroacetyl hydrazide compounds have good pharmacological properties, and the results of clinical trials are now submitting to the FDA. In the present invention, tetramethyl pyrazine (TMP), the main active ingredient in the traditional Chinese medicine chuanxiong, is introduced into J147 to obtain a new compound T-006, thus giving T-006 a multiple mechanism of both J147 and TMP for multifunctional treatment of AD activity.

SUMMARY OF THE INVENTION

The present invention provided a trifluoroacetyl hydrazide compound which has a strong inhibition of glutamate receptors, activation of MEF2 transcriptional activity, enhance of cognitive ability, promotion of neural differentiation and clearance of free radicals, and has a better protective effect on cells especially nerve cells.

The present invention also provides a method of preparation of the trifluoroacetyl hydrazide compound.

The present invention provided also method of the trifluoroacetyl hydrazide compound for prevention or treatment of diseases and use in manufacture of a supplement or medicament for prevention or treatment of diseases.

The present invention provided a trifluoroacetyl hydrazide compound of formula I, or a pharmaceutically acceptable salt thereof:

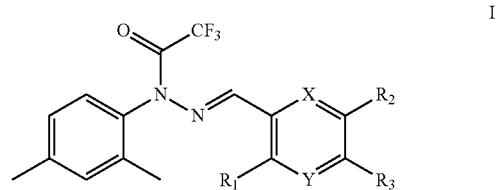

wherein:
$R_1$, $R_2$ and $R_3$ are each independently hydrogen, OH, $NH_2$, COOH, alkyl, aryl, heterocyclic aryl, ester group, amino group or carbamic acid ester group, but cannot be hydrogen at the same time;
X and Y are each independently C, N, O or S, but cannot be C at the same time.

In some embodiments, in the preferred compounds of formula I, X and Y are both N.

In a preferred compound of formula I, X and Y are both N, and $R_1$, $R_2$ and $R_3$ are the same or different and are each independently alkyl, aryl or heteroaryl group.

In some embodiments, the alkyl group is a lower alkyl group, such as methyl, ethyl, n-propyl, n-butyl, n-pentyl, n-hexyl, n-heptyl, n-octyl, isopropyl, sec-butyl, isobutyl, t-butyl, neopentyl, cyclopropyl, cyclobutyl, cyclopentyl or cyclohexyl; especially methyl, ethyl, n-propyl, isopropyl, n-butyl, isobutyl, or tert-butyl group.

In further preferred compounds of formula I, X and Y are both N, and $R_1$, $R_2$ and $R_3$ are methyl, that is, the compound has a structure of formula II.

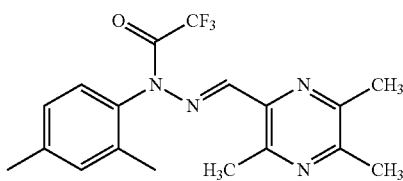

II

The compound of the invention has a good protective effect on cells especially nerve cells, and can be used to prepare prophylactic or therapeutic medicaments with cytoprotective effects. The medicaments may include a compound having aforementioned structure or a pharmaceutically acceptable salt thereof, to be administered in an effective therapeutic amount to a patient.

The present invention provides a compound which has multifunctional mechanisms such as of strong inhibition of glutamate receptors, activation of MEF2 transcriptional activity, enhance of cognitive ability, promotion of neural differentiation and clearance of free radicals, and has a better protective effect on cells especially nerve cells. The compound can be used to prepare prophylactic or therapeutic medicaments with cytoprotective effects, for the prevention or treatment of diseases related to glutamate receptor activation, MEF2 disorder, oxidative stress injury or excessive free radicals generation, or neurodegenerative diseases. The diseases include, for example, neurodegenerative diseases such as Alzheimer's disease, Parkinson's disease and stroke, and the free radicals related diseases such as heart disease and diabetes. A method of preventing or treating such diseases comprises administering to a patient a medicament prepared by a compound described herein, wherein the medicament includes an effective therapeutic amount of a compound having the structure described above or a pharmaceutically acceptable salt thereof.

The following terms and phrases as used herein are intended to have the meanings as described below.

As used herein, the term "alkyl" refers to an unsubstituted or substituted straight-chain, branched-chain, or cyclic-chain having up to 10 carbon atoms; the straight-alkyl includes, for example, methyl, ethyl, n-propyl, n-butyl, n-pentyl, n-hexyl, n-heptyl and n-octyl; the branched-chain alkyl includes, for example, isopropyl, sec-butyl, isobutyl, tert-butyl, neopentyl; the cyclic alkyl ("cycloalkyl") includes, for example, cyclopropyl, cyclobutyl, cyclopentyl and cyclohexyl; and further an alkyl group may be substituted with one or more substituents, which include, but are not limited to, $NH_2$, $NO_2$, $N(CH_3)_2$, $ONO_2$, F, Cl, Br, I, OH, $OCH_3$, $CO_2H$, $CO_2CH_3$, CN, aryl, and heteroaryl. The term "alkyl" may also refer to an unsubstituted or substituted straight-chain, branched-chain, or cyclic alkyl having up to 10 carbon atoms, which further contains in the chain at least one heteroatom (e.g., nitrogen, oxygen, or sulfur); the above straight-chain alkyl includes, for example, $CH_2CH_2OCH_3$, $CH_2CH_2N(CH_3)_2$ and $CH_2CH_2SCH_3$; the branched-chain alkyl includes, for example, $CH_2CH(OCH_3)CH_3$, $CH_2CH(N(CH_3)_2)CH_3$ and $CH_2CH(OCH_3)CH_3$, the cyclic alkyl includes, for example, $CH(CH_2CH_2)_2O$, $H(CH_2CH_2)_2NCH_3$ and $CH(CH_2CH_2)_2S$, and further the alkyl can be substituted by one or more substituents which include but not limited to $NH_2$, $NO_2$, $N(CH_3)_2$, $ONO_2$, F, Cl, Br, I, OH, $OCH_3$, $CO_2H$, $CO_2CH_3$, CN, aryl, and heteroaryl.

As used herein, the term "aryl" refers to an unsubstituted or substituted aromatic group, carbocyclic group and heteroaryl. The aryl can be either a monocyclic group or a fused polycyclic group; for example, phenyl is a monocyclic aryl, and naphtyl is a fused polycyclic aryl. The aryl can be substituted by one or more substituents, which include but not limited to $NH_2$, $NO_2$, $N(CH_3)_2$, $ONO_2$, F, Cl, Br, I, OH, $OCH_3$, $CO_2H$, $CO_2CH_3$, CN, aryl, and heteroaryl.

The term "heteroaryl" refers to The heteroaryl relates to substituted or an unsubstituted monocyclic or polycyclic group, where the ring contains at least one heteroatom, such as nitrogen, oxygen and sulfur. For example, a typical heteroaryl includes one or more nitrogen atoms such as in tetrazolyl, pyrrolyl, pyridyl (e.g., pyrid-4-yl, pyrid-3-yl, pyrid-2-yl), pyridazinyl, indyl, quinolyl (e.g., quinol-2-yl, quinol-3-yl), imidazolyl, isoquinolyl, pyrazolyl, pyrazinyl, pyrimidinyl, pyridonyl and pyridazinyl; a typical heteroaryl includes at least one oxygen atom such as in fur-2-yl, fur-3-yl and benzofuryl; a typical heteroaryl includes at least one sulfur atom such as in thienyl and benzothienyl; a typical heteroaryl containing more than one kind of heteroatoms includes furoazetidinyl, oxazolyl, isoxazolyl, thiazolyl and phenothioxinyl. The heteroaryl can be substituted by one or more substituents which include but not limited to $NH_2$, $NO_2$, O-alkyl, NH-alkyl, $N(alkyl)_2$, NHC(O)-alkyl, $ONO_2$, F, Cl, Br, I, OH, $OCF_3$, $OSO_2CH_3$, $CO_2H$, $CO_2$-alkyl, CN, aryl, and polyaryl. Furthermore, the heteroaryl also includes those with a heteroatom in the ring being oxidized, for example, to form N-oxide, ketone, or sulfone.

The phrase "pharmaceutically acceptable," as used herein, means that there is no unacceptable toxicity in a salt or excipient. The pharmaceutically acceptable salts include inorganic anions such as those of chloride, bromide, iodide, sulfate, sulfite, nitrate, nitrite, and phosphate and phosphite, and organic anions such as those of acetate, propionate, cinnamate, tosylate, citrate, lactate and gluconate. In adding to the pharmaceutically acceptable excipients described herebelow, see also: E. W. Martin, in Remington's Pharmaceutical Sciences Mack Publishing Company (1995), Philadelphia, Pa., $19^{th}$ ed.

The compounds of the invention include TMP trifluoroacetyl hydrazide compounds of formula I or II. The compounds of formula I or II has properties to inhibit glutamate receptors, enhance the transcriptional activity of MEF2, strengthen free radical scavenging effect, and has goof protective effect on cells especially nerve cells. The compounds can be used to prepare prophylactic or therapeutic medicaments with cytoprotective effects, to prevent or treat diseases related to glutamate receptor activation, MEF2 disorder and/or excessive radical generation. These diseases usually include neurodegenerative diseases or free radical related diseases, such as Parkinson's disease, Alzheimer's disease, dementia, hypertension, diarrhea, depression, asthma and allergy; also include cholinesterase related diseases, such as Alzheimer's disease, Parkinson's disease, Huntington's disease, muscular atrophic lateral sclerosis, myasthenia gravis, glaucoma, Alzheimer's disease, hyperthyroidism, hypertension, Bronchial asthma, type IV hyperlipoproteinemia and renal failure; also include diseases related to oxidative stress injury or excessive free radicals generation, such as stroke, brain trauma, epilepsy, Parkinson's disease, Huntington's disease, amyotrophic lateral sclerosis, Alzheimer's disease, hypoxic-ischemic brain damage, cerebral hemorrhage Dementia, ischemic heart disease, vascular embolism, atherosclerosis, hypercholesterolemia, emphysema, cataract, diabetes, acute pancreatitis, alcohol-induced liver disease, kidney damage, cancer; can also be used to prevent and treat neurodegenerative diseases such as cerebral ischemia, Parkinson's disease, Alzheimer's disease, muscular atrophic lateral sclerosis, ataxia telangiectasia, bovine spongiform encephalopathy, Creutzfeldt-Jakob disease, Huntington chorea, cerebellar atrophy, multiple sclerosis, primary lateral sclerosis and spinal muscular dystrophy.

The compounds as described herein may be administered to a patient in the form of a pharmaceutical acceptable salts or complex drugs. A certain component needs to be mixed with an appropriate carrier or excipient to form a pharmaceutical composition to reach a desirable therapeutically effective amount. "The effective therapeutic amount" refers to the necessary amount of a compound described herein, or of a combination of compounds described herein to attain a therapeutic effect.

The compounds as described herein can be prepared in different dosage forms, which include solid, semi-solid, liquid, and aerosol (*Remington's Pharmaceutical Sciences*, Mack Publishing Company (1995), Philadelphia, Pa., 19$^{th}$ ed). These dosage forms can be further divided into more specific forms, including tablet, pill, sugar lozenge, granule, gel, paste, solution, suppository, injection, inhalant and spray. These dosage forms can be used for local or systemic administration and for immediate-release or sustained release. There are many routes of administration of these drugs, which include oral, buccal, rectal, peritoneal, intraperitoneal, transdermal administration, subcutaneous and endotracheal administrations When the compound or composition as described herein is applied in a dosage form of injection, the compound or composition can be prepared, by using a water-soluble or lipid-soluble solvent, into a solution, suspension or emulsion. The lipid-soluble solvent can be, for example, plant oil, synthetic fatty acid glyceride, higher fatty acid ester and/or proylene glycol. The compounds as described herein are more readily dissolved in Hank's solution, Ringer's solution or physiological saline.

When applied through oral administration, the compound or composition as described herein can be prepared through certain common techniques into a complex by adding a pharmaceutical acceptable excipient. Such excipients can be used to prepare these compounds into different dosage forms, such as tablet, pill, suspension, and gel. There are many ways for oral preparation, for example, by mixing the compound and the solid excipient, grinding fully the resulting mixture, adding appropriate auxiliary agents, and processing the mixture into particles. The auxiliary agents, which can be used for oral preparation, include, for example, sugars such as lactose, sucrose, mannitol, or sorbitol; celluloses such as corn starch, wheat starch, potato starch, gelatin, gummi tragacanthae, methyl cellulose, hydroxypropylmethyl-cellulose, sodium carboxymethyl cellulose, and polyethylene pyrrole ketones.

The compounds as described herein can be prepared also in the form of spray, which can be achieved by using a pressurizer and a sprayer or dry powder inhaling device. Suitable spray agents used for spraying include, for example, dichlorodifluoromethane, fluorine chloroform, dichloro-tetrafluoroethane, carbon dioxide, and dimethyl ether. The amount of spray delivered from a sprayer can be controlled by the adjustment of the injecting valve of the sprayer.

The dosage forms as described herein are all related to the therapeutically effective amount of the compounds of the invention. The therapeutically effective amount of the compounds as described herein may depend on specific conditions of patients under the treatment. To determine the appropriate dose, various factors much be taken into account, for example, the route of administration to be used, weight and conditions of the patient to be treated, and observation and subjective judgment made by the prescribing physician. The therapeutically effective amount is usually determined by an experienced prescribing physician.

While the effective therapeutic dose of the compounds and their derivatives as described herein may vary depending on the patient's conditions, an appropriate dosage range is usually 10 mg to 10 g.

Compared with the prior art, the invention has the following advantageous characteristics: the compounds as described herein have novel structures and multiple mechanisms of activity, and they can be used to inhibit glutamate receptors, enhance MEF2 activity and improving free radical scavenging activity, and has a better protective effect on cells, especially nerve cells. The compounds can be used to prepare prophylactic or therapeutic drugs with cytoprotective effects, for the treatment of diseases related to glutamate receptor, MEF2 or free radicals and the like. Such diseases are commonly referred to as neurodegenerative diseases, such as Alzheimer's disease, Parkinson's disease, stroke and so on, as well as diseases related to free radicals such as heart disease, diabetes and so on.

DETAILED DESCRIPTION OF EMBODIMENTS

Some specific embodiments or examples of the present invention will be described below. It will be understood that these specific embodiments or examples are only used for further explanation of the invention, rather than to limit the scope of the inventive subject matters as defined by the claims.

EXAMPLE 1

Figure 1:
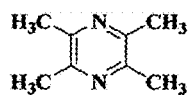
FIG. 1. Structure of compounds of TMP and T-006.
Figure 1:
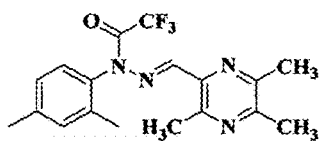
Figure 2:
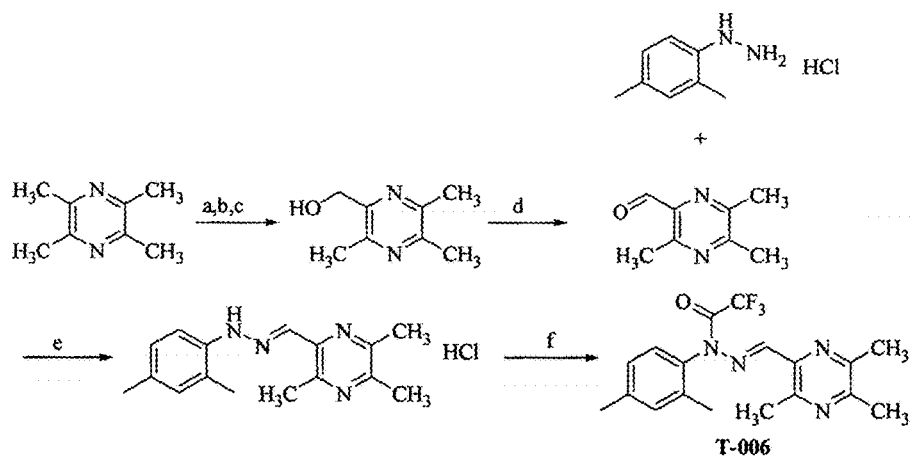
FIG. 2. Synthetic scheme of compound T-006.

Synthesis of Compound T-006 (FIG. 2)

In 10 mL of methanol was dissolved 2,4-dimethylphenyl-hydrazide hydrochloride (1.72 g, 10 mmol). To the solution, 3,5,6-trimethylpyrazine-2-carbaldehyde (1.50 g, 12 mmol) was added with an ice-bath under the protection of $N_2$. After the mixture was stirred for 10 min, a lot of brick red precipitate showed and the reaction was then complete. The mixture was filtered through a suction funnel, and the brick red solid was transferred to a vacuum oven to be dried for using directly in the next reaction step of the reaction. The red brick intermediate (3.04 g, 10 mmol) was dissolved in 25 mL of methanol, and 1.68 ml of anhydrous triethylamine and 1.7 ml of trifluoroacetic anhydride were added respectively with an ice-bath under the protection of $N_2$, and the reaction was run for 30 minutes. The reaction was monitored by TLC till completion. The resulting material was extracted with Ethyl acetate, dried over anhydrous Na2SO4, separated by a silica gel column (ethyl acetate:petroleum ether=1:3) to get T-006 as a light yellow solid (3.25 g, 89.3%). ESI-MS: $[M+H]^+$ m/z 365.1. $^1$H-NMR (CDCl$_3$, 300 MHz) δ: 2.1 (s, 3H), 2.42 (s, 3H), 2.46 (s, 3H), 2.54 (s, 3H), 2.85 (s, 3H), 7.08 (d, j=7.05 Hz, 1H), 7.24 (d, J=7.21 Hz, 1H), 7.25 (s, 1H), 7.55 (s, 1H); Anal. ($C_{18}H_{19}F_3N_4O$) C, H, C, found C, 59.44%; H, 5.319%; N, 15.23%; requires: C, 59.33%; H, 5.26%; N, 15.38%.

EXAMPLE 2

Figure 3:
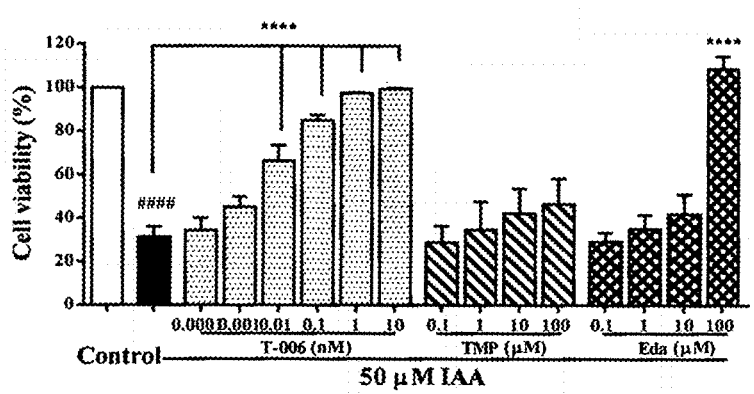
FIG. 3. Protective effects of T-006 on IAA induced PC12 cell injury.

Protective Effects of T-006 on IAA-induced PC12 Cell Injury. (FIG. 3)

PC12 cells were seeded on a 96-well plate and inoculated in a 5% $CO_2$ incubator at 37° C. for 24 hours. Then 100 μl of IAA (50 μM) was added for induction for 2 hours. Two hours later, the medium was aspirated, and each of the compounds (T-006, TMP, Edaravone) was added and the cells were cultured for 24 hours. After 24 hours of incubation, MTT was added to each well. Four hours later, the absorbance was measured at 570 nm using a microplate reader. The results were shown in FIG. 3: T-006 had a significant protective effect on IAA-induced PC12 cell injury, and was much stronger than that of the parent compound TMP and Edaravone. Compared with the IAA group, ****$P<0.0001$.

EXAMPLE 3

Figure 4:
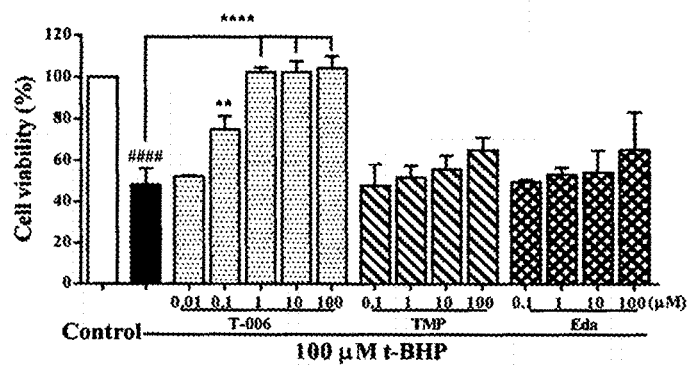
FIG. 4. Protective effects of T-006 on t-BHP induced PC12 cell injury.

Protective Effect of T-006 on t-BHP-induced PC12 Cell Injury (FIG. 4)

PC12 cells were seeded on a 96-well plate and inoculated in a 5% $CO_2$ incubator at 37° C., for 24 hours. Then each compound (T-006, TMP, Edaravone) was added in different concentration gradients to pre-incubated for 2 hours. Two hours later, the medium was aspirated, and 100 μl t-BHP (100 μM) was added to each well except those of the control group, then the cells were cultured in an incubator for 24 hours. Four hours later, MTT was added into each of the wells, and the absorbance was measured at 570 nm using a microplate reader. The results were shown in FIG. 4: T-006 had a significant protective effect on t-BHP-induced PC12 cell injury, and the effect is much stronger than that of the parent compound TMP or Edaravone. Compared with t-BHP group, ****$P<0.0001$.

EXAMPLE 4

Figure 5:
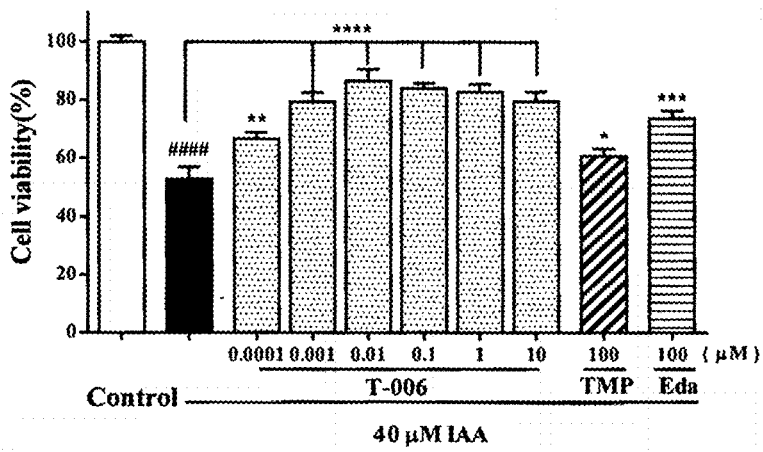
FIG. 5. Protective effects of T-006 on IAA induced cortical neuronal injury.

Protective Effects of T-006 on IAA-induced Cortical Neuronal Injury (FIG. 5)

Cortical neurons of E16-18 day SD fetal rat were seeded on a 96-well plate and inoculated in a 5% $CO_2$ incubator at 37° C. for 8 days. On day 8, each of the compounds (T-006, TMP, Edaravone) was added with different concentration gradients, and 50 μl IAA (40 μM) was added to each well except those of the control group. Then the neurons were set to incubator to cultivate for 24 hours, and then MTT was added to each well. Four hours later, the absorbance was measured at 570 nm using a microplate reader. The results were shown in FIG. 5: T-006 had a significant protective effect on IAA-induced cortical neuronal injury, and was much stronger than that of the parent compound TMP and Edaravone. Compared with the IAA group, ****$P<0.0001$.

EXAMPLE 5

Figure 6:
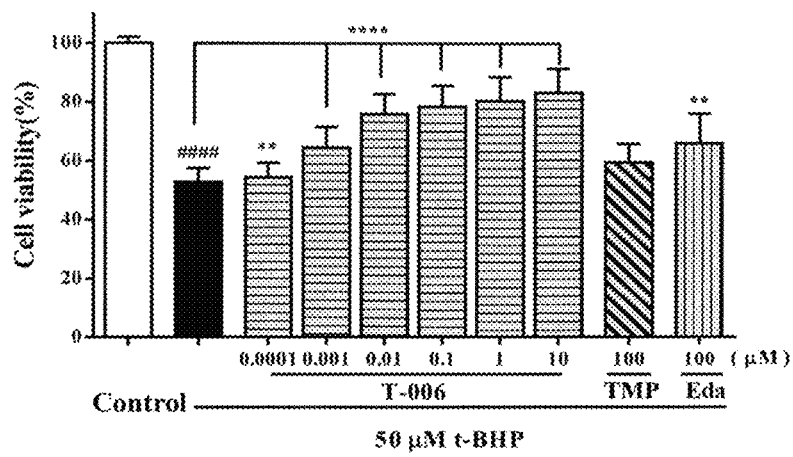
FIG. 6. Protective effects of T-006 on t-BHP induced cortical neuronal injury.

Protective Effects of T-006 on t-BHP-induced Cortical Neuronal Injury (FIG. 6)

Cortical neurons of E16-18 days SD fetal rat were seeded on a 96-well plate and inoculated in a 5% $CO_2$ incubator at 37° C. for 8 days. On day 8, each of the compounds (T-006, TMP, Edaravone) was added with different concentration gradients, and 50 μl IAA (40 μM) was added to each well except those of the control group. The neurons were set to incubator to cultivate for 24 hours, and then MTT was added to each well. Four hours later, the absorbance value was measured at 570 nm using a microplate reader. The results were shown in FIG. 6: T-006 had a significant protective effect on t-BHP-induced cortical neuronal injury, and was much stronger than that of the parent compound TMP and Edaravone. Compared with the t-BHP group, ****$P<0.0001$.

EXAMPLE 6

Figure 7:
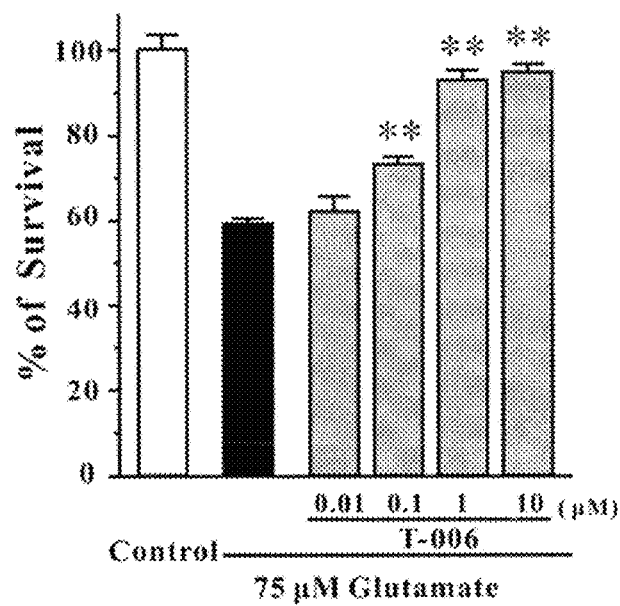
FIG. 7. Protective effects of T-006 on glutamate induced cerebellar granule injury.

Protective Effects of T-006 on t-BHP-induced Cerebellar Granule Injury (FIG. 7)

Primary cerebellar granule cells, extracted from 7-8 day, 15-20 g SD fetal rat, were seeded on a 96-well plate and inoculated in a 5% $CO_2$ incubator at 37° C. for 8 days. On day 8, 90 μL of the compound (T-006) was added with different concentration gradients, then the cells were set to an incubator to cultivate for 2 hours. Then 10 μL of glutamate (final concentration of 75 μM) was added to each well except those of the control group. The cells were set to incubator to cultivate for 24 hours, and then MTT was added to each well. Four hours later, the absorbance value was measured at 570 nm using a microplate reader. The results were shown in FIG. 7: T-006 had a significant protective effect on glutamate-induced primary cerebellar granule injury, and showed a better concentration-dependent. Compared with the glutamate group, **P<0.01.

EXAMPLE 7

Figure 8:
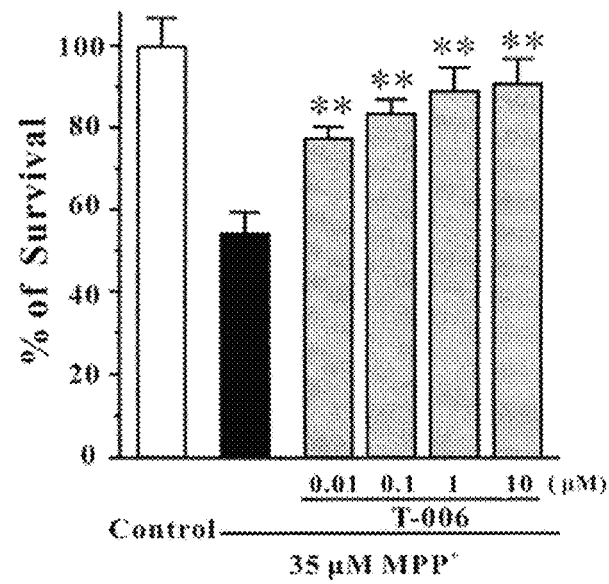
FIG. 8. Protective effects of T-006 on MPP$^+$ induced cerebellar granule injury.

Protective Effects of T-006 on $MPP^+$-induced Cerebellar Granule Injury (FIG. 8)

Primary cerebellar granule cells, extracted from 7-8 days, 15-20 g SD fetal rat, were seeded on a 96-well plate and inoculated in a 5% $CO_2$ incubator at 37° C. for 8 days. On day 8, 90 μL of the compound (T-006) was added with different concentration gradients, then the cells were set to an incubator to cultivate for 2 hours. Then 10 μL of $MPP^+$ (final concentration of 35 μM) was added to each well except those of the control group. The cells were set to incubator to cultivate for 24 hours, and then MTT was added to each well. Four hours later, the absorbance value was measured at 570 nm using a microplate reader. The results were shown in FIG. 8: T-006 had a significant protective effect on $MPP^+$-induced Primary cerebellar granule injury, and showed a better concentration-dependent. Compared with the $MPP^+$ group, **P<0.01.

EXAMPLE 8

Figure 9:
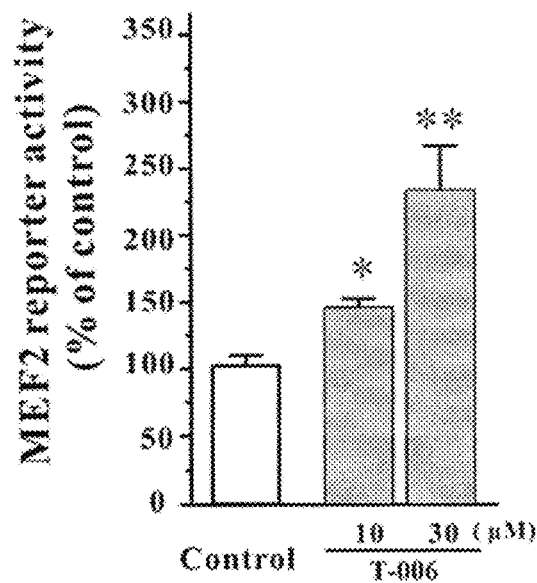
FIG. 9. T-006 can enhance MEF2 activity in PC12 cells.

T-006 Activates MEF2 Transcription Activity in PC12 Cells (FIG. 9)

The PC12 was transfected by cloning the MEF2 reporter gene pGreenFire1TM-MEF2-EF1 lentivector. Stable transfected PC12 cells, as cultured in a conventional manner, were seeded on a 96-well plate with T-006 added in different concentrations, were incubated for 24 h. The activity was measured by the Luciferase reporter assay kit (Promega, USA). The results were shown in FIG. 9: T-006 significantly activates ME12 transcriptional activity in PC12 cells. Compared with the IAA group, **P<0.01.

EXAMPLE 9

Figure 10A:
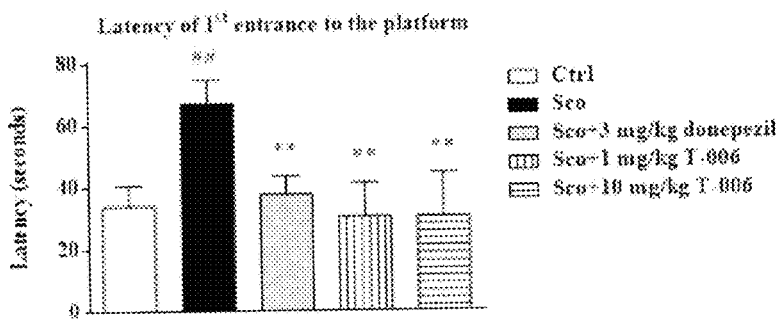
FIGS. 10A and 10B. T-006 can significantly improve scopolamine-induced memory impairment in mice.
Figure 10B:
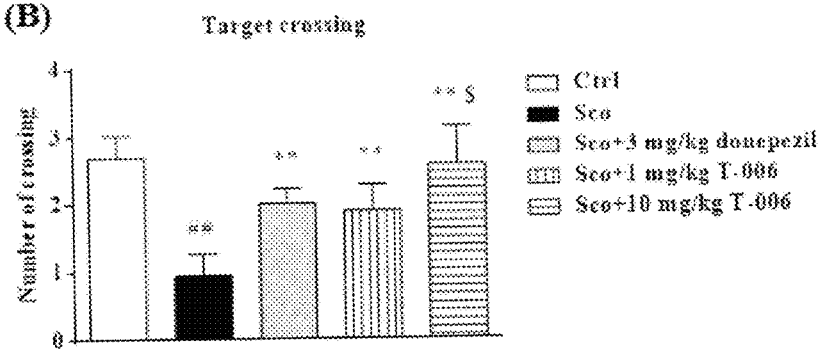

T-006 can Significantly Improve Scopolamine-induced Memory Impairment in Mice (FIGS. 10A and 10B)

In this example, Kunming mice were selected and divided into normal control group (Ctrl), Scopolamine group (Sco), Donepezil treatment group (Sco+3 mg/kg donepezil), 1 and 10 mg T-006 treatment group (Sco+1 mg/kg T-006 and Sco+10 mg/kg T-006). Intragastric administration was performed for two weeks, and after the final administration water maze test was conducted for 4 days. Thirty minutes before the test, abdominal injection of scopolamine (1 mg/kg) and model were performed. On day 5, space search test was conducted, and data were expressed as Mean±SD (n=9 per group). The results were shown in FIG. 10A and FIG. 10B: Scopolamine-induced memory of mice was significantly impaired, the first incubation period of the platform was significantly prolonged, the number of times through the target platform decreased (compared with the normal control group, ## p<0.01); 1 and 10 mg/kg T-006 treatment group and 3 mg/kg donepezil treatment group significantly improved the memory impairment induced by scopolamine (compared with the scopolamine model group, **p<0.01); and 10 mg/kg T-006 group was significantly better than 3 mg/kg donepezil group ($p<0.05).

EXAMPLE 10

Figure 11:
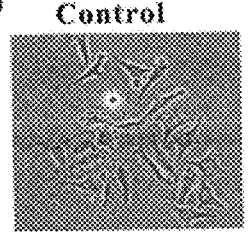
FIG. 11. T-006 can promote PC12 cells being differentiated into neurons with synapse growing and elongating.
Figure 11:
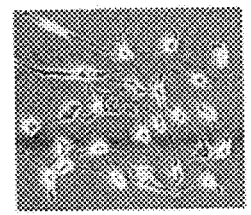
Figure 11:
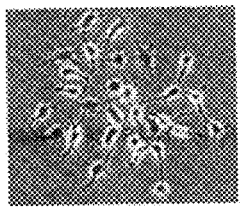
Figure 11:
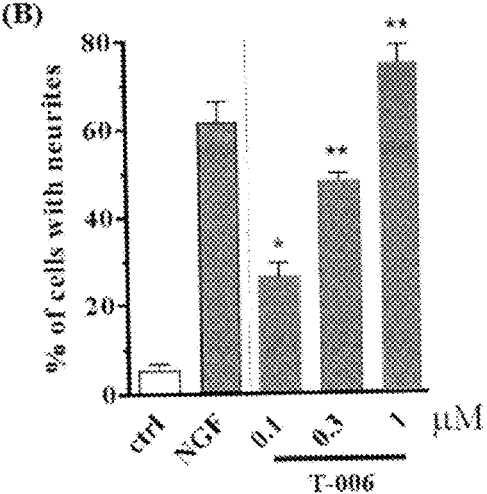
Figure 12A:
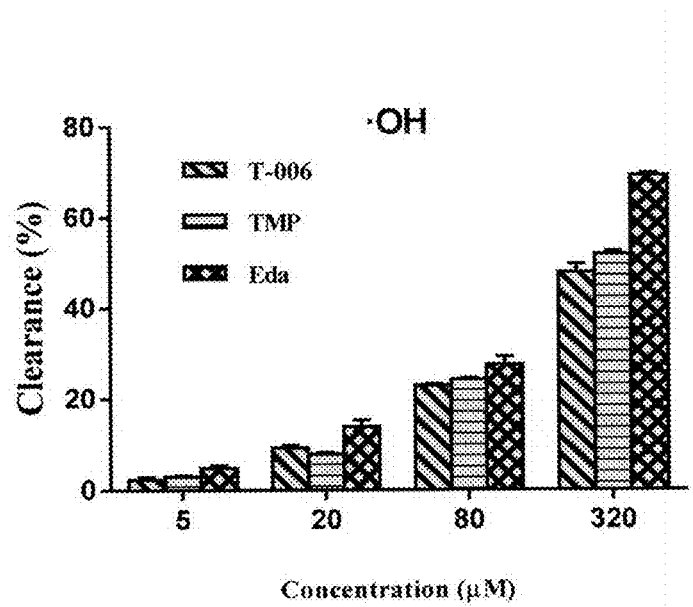
FIGS. 12A to 12D. Scavenging effect of T-006 on free radicals.
Figure 12B:
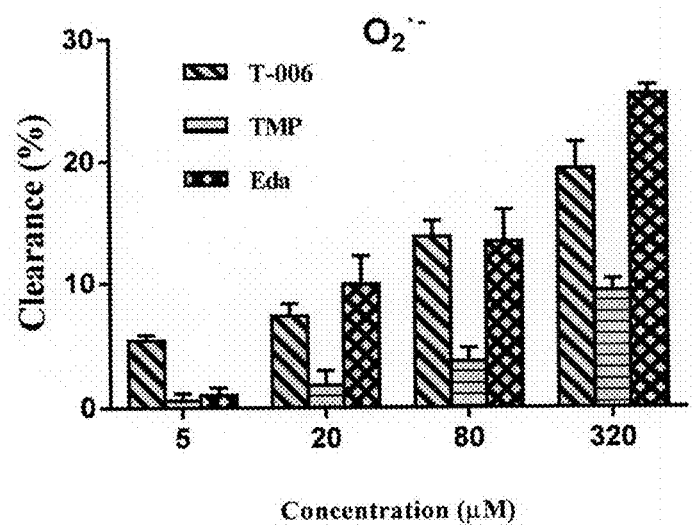
Figure 12C:
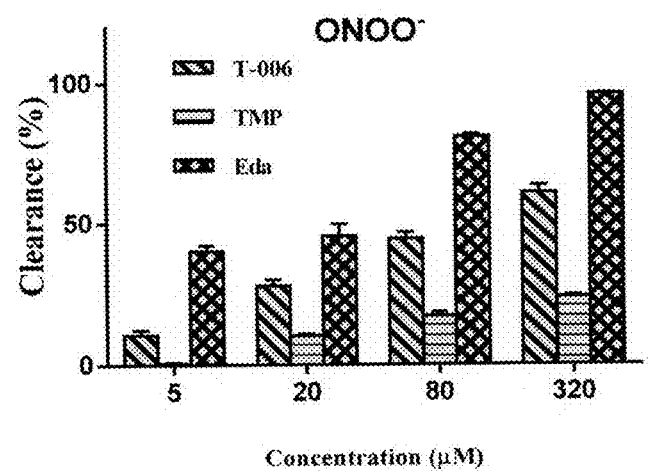
Figure 12D:
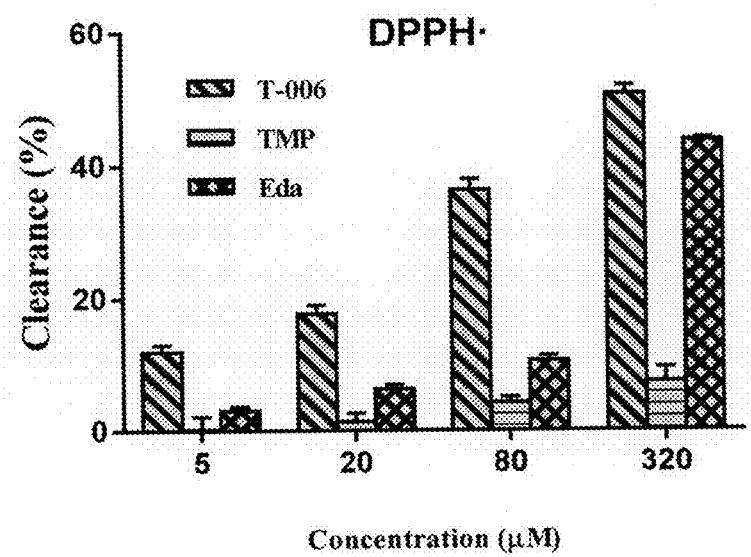

T-006 can Promote PC12 Cells being Differentiated into Neurons with Synapse Growing and Elongating (FIG. 11)

PC12 cells were seeded on 6-well plate and inoculated in a 5% $CO_2$ incubator at 37° C. for 24 hours. Control group was unchanged; NGF control group: serum-free F-12K+50 ng/mL NGF; drug treatment group: serum-free F-12K with different concentrations of T-006. After 72 hours of incubation, picture was taken under an inverted microscope with 5 shoots at random for each hole. If the cell synapse length is more than 2 times the cell, it can be regarded as cell differentiation and synapse formation. The results were shown in FIG. 11: T-006 and positive control NGF could significantly promote differentiation of PC12 cells into neurons, synapse formation and growth, and showed a better concentration-dependent. Compared with the control group, **P<0.01.

EXAMPLE 11

Scavenging Effects of the Compound on $OH^-$, $O_2.^-$, ONOO—, and DPPH Free Radicals (FIGS. 12A-12D)

Hydroxyl radical (OH.): o-Phenanthroline-metal ion-$H_2O_2$ were used to produce hydroxyl radicals via Fenton reaction ($H_2O_2+Fe^{2+}\rightarrow.OH+H_2O+Fe^{3+}$), to promote the oxidation of o-phenanthroline-$Fe^{2+}$ to o-phenanthroline-$Fe^{3+}$, resulting in an aqueous solution disappearance at the maximum at the wavelength of 440 nm so that the clearance rate was calculated. The specific steps are: In a 48-well plate was added 300 μL of double distilled water (blank control) or T-006, TMP, Edaravone in different concentrations (DMSO was used to prepare a 10 mM stock solution which was then diluted with double distilled water to 4 μM, 20 μM, 80 μM, 320 μM), and 50 μL of 1.0 mM o-phenanthroline (1.0 mM dissolved in 50 mM NaCl solution) was added and then mixed with 125 μL of 1.0 mM $H_2O_2$ and 125 μL 2.0 mM $Fe^{2+}$, respectively, and BioTek Synergy HT was used to measure the percentage of absorbance decreasing at 440 nm in 100 seconds. The hydroxyl radical scavenging rate was calculated as: clearance rate (%)=$[1-(A_0-A_{100})/A_0]\times 100\%$, $A_0$ and $A_{100}$ being the absorbance values at 0 seconds and 100 seconds, respectively.

Superoxide anionic radicals ($O_2.^-$): Pyrogallol autoxidation method was used, and the specific steps are: to a 48 well plate was added 250 μL of 50 mM Tris-HCl buffer (pH 8.2), 300 μL of double distilled water (control group) or T-006, TMP, Edaravone in different concentrations (DMSO was used to prepare a 10 mM stock solution which was then diluted with double distilled water to 4 μM, 20 μM, 80 μM, 320 μM). Then 50 L of 2.0 mM of pyrogallol was added being mixed with a vortex mixer. At a wavelength of 320 nm, the absorbance of the blank control group was recorded every 30 seconds using a BioTek Synergy HT microplate reader for 30 minutes. The absorbance of the samples was measured under the same conditions, and the oxidation rate was the increment of absorbance per minute. By using linear regression method with time (seconds) as the abscissa and absorbance value as the ordinate, the linear relationship between absorbance value and time was obtained to calculate the pyrogallol autoxidation rate. The results are expressed in increments of dA/dt of the absorbance value per second, ie the a value in $R^2$ in the linear regression equation of y=ax+b. Clearance rate (%)=(dA/dt−dAs/dt)/(dA/dt), wherein dA/dt is the autoxidation rate of pyrogallol in the absence of sample, dAs/dt is the rate of pyrogallol in the presence of the sample.

Peroxynitrite free radicals ($ONOO^-$): The peroxynitrite free radical (ONOO—) can be measured by SIN-1 simulation of the process of ONOO— generation in the body. SIN-1 decomposes under weak alkaline conditions (PBS pH 7.4), which can then simultaneously produce superoxide anion radical ($O_2.^-$) and nitric oxide free radical (NO.), and both of which instantaneously produce peroxynitrite Anion ($ONOO^-$). ONOO— reacts with luminal by oxidization and excitation with emission at 425 nm. The luminous intensity can be measured to determine the generation of ONOO—. Antioxidant (AH) competes with Luminol (L) in the reaction with ONOO—, and thus reduces the reaction of ONOO— with LH—, and then reduces the luminous intensity. The luminous intensity is inversely correlated with the antioxidating capacity of the antioxidant, so that quantitative analysis can be made based on the change of the luminescence intensity before and after the reaction. The specific steps of the test are: In a 3 mL round bottom photometer tube were added 300 μL 0.1 M PBS buffer solution (pH 7.4), 50 μL 1 mM Luminol solution, 100 μL PBS or T-006, TMP, Edaravone in different concentrations DMSO was used to prepare a 10 mM stock solution, which was then diluted into 4 μM, 20 μM, 80 μM, 320 μM). Then 50 μL of 3 mg/mL SIN-1 hydrochloride solution was added and mixed with a vortex mixer. With the blank group as control, the photometric tube was placed with the temperature being controlled at 37° C., and the luminous value was recorded every 100 s with a luminometer continuously for 2000 s, and each measurement of the concentration is repeated at least three times and averaged. The clearance rate is calculated by the following formula: Clear rate rate (%)=($A_{ctrl}-A_{sample}$)/$A_{ctrl}$×100.

1.1-Diphenyl-2-phenylhydrazide radicals (DPPH): The test of 1.1-Diphenyl-2-phenylhydrazide radicals (DPPH) spectrophotometry is based on that DPPH has a strong absorption at 517 nm, and has a deep violet color in methanol solution. When free radical scavenger is present, the absorption gradually disappears due to single electron pairing, and the extent of color fading is correlated quantitatively to the number of electrons received by the DPPH. Therefore, by detecting the change of optical absorbance of DPPH in with the samples in different concentrations, the clearance rate can be used as an indication of the free radical scavenging ability. The specific steps of the test are: Onto a 96 well plate was added 100 μL of T-006, TMP, Edaravone (dissolved in DMSO to make a 10 mM stock solution and then diluted with double distilled water to 4 μM, 20 μM, 80 μM, 320 μM) in different concentrations or 100 μL methanol (as blank control group), then quickly added with 100 μL of 100 μM DPPH solution in methanol (50 μM of final concentration), each sample concentration was repeated in 3-5 holes, vibrated evenly and then placed at room temperature under dark condition for one hour. The absorbance values were then measured at 517 nm using a microplate reader. Clearance rate (%)=($A_{ctrl}-A_{sample}$)/$A_{ctrl}$×100.

EXAMPLE 12

Figure 13A:
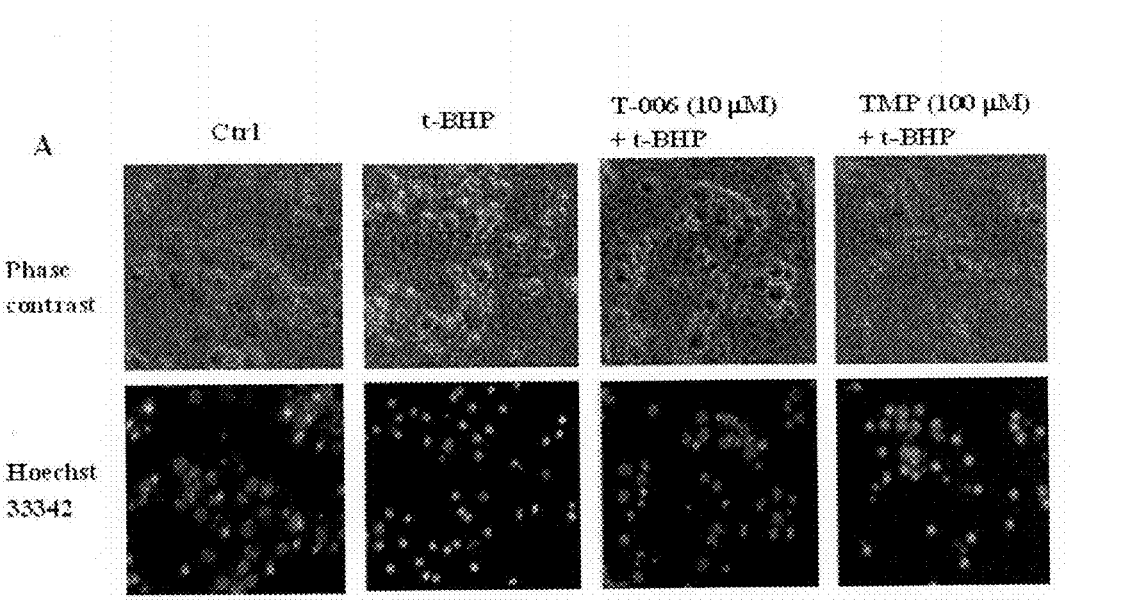
FIGS. 13A to 13C. T-006 reduced the t-BHP-induced apoptosis of PC12 cells.
Figure 13B:
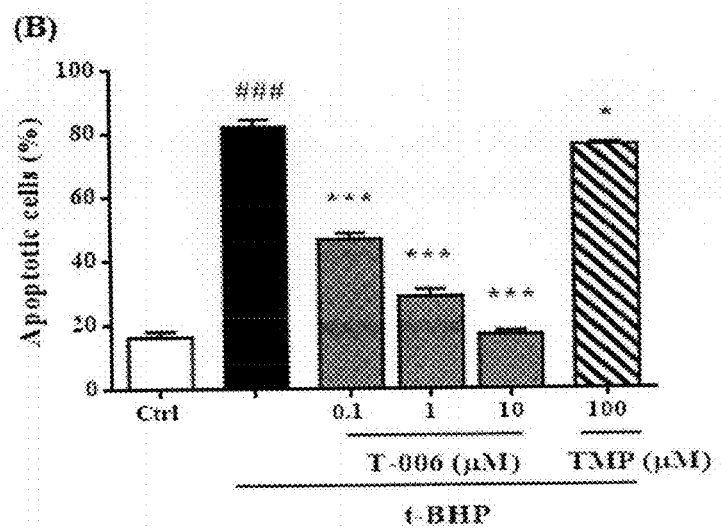
Figure 13C:
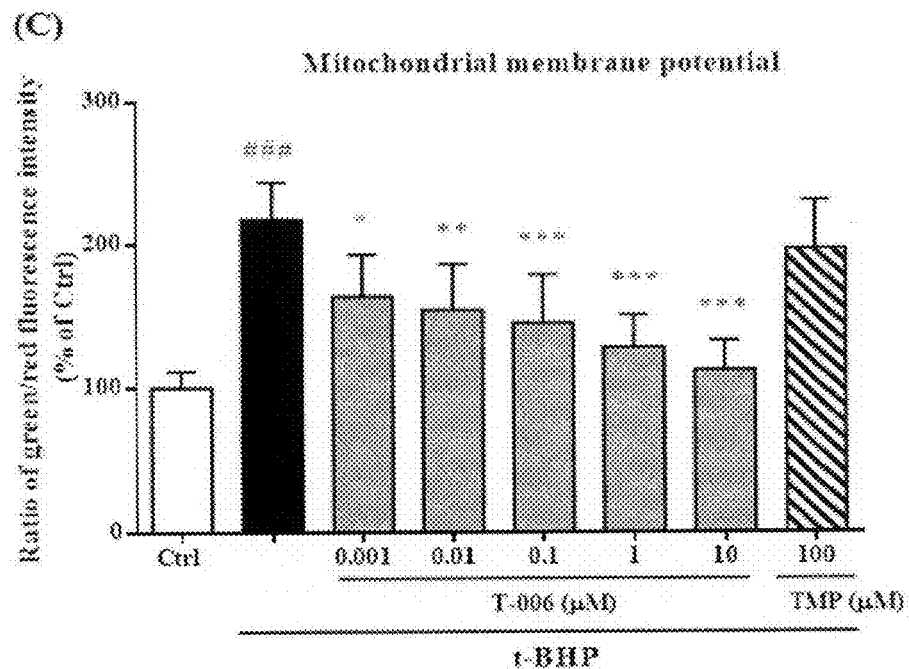
Figure 14A:
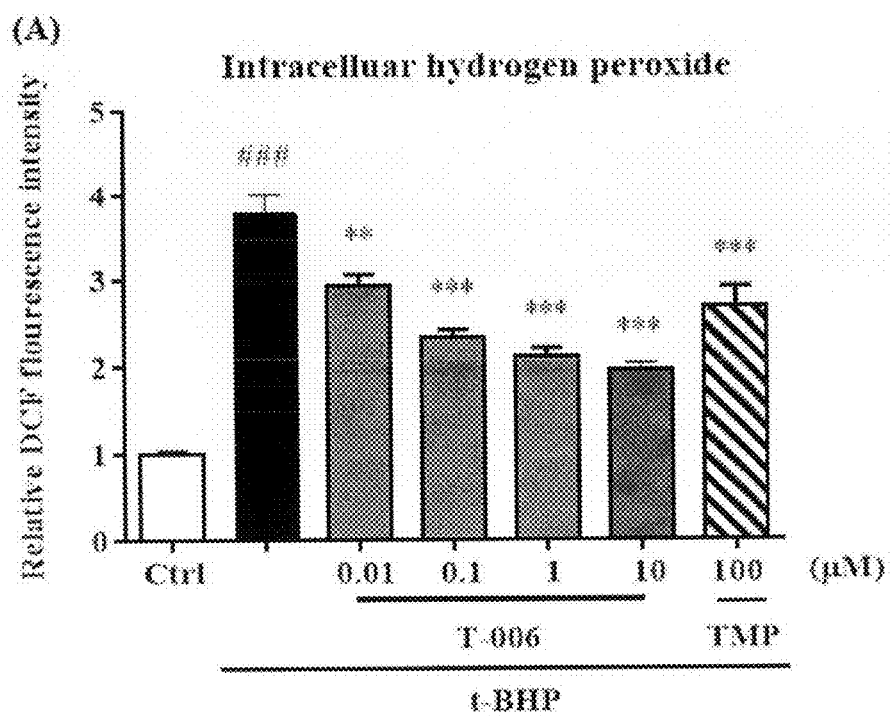
FIGS. 14A to 14D. T-006 reduced the t-BHP-induced increase of ROS and RNS in PC12 cells.
Figure 14B:
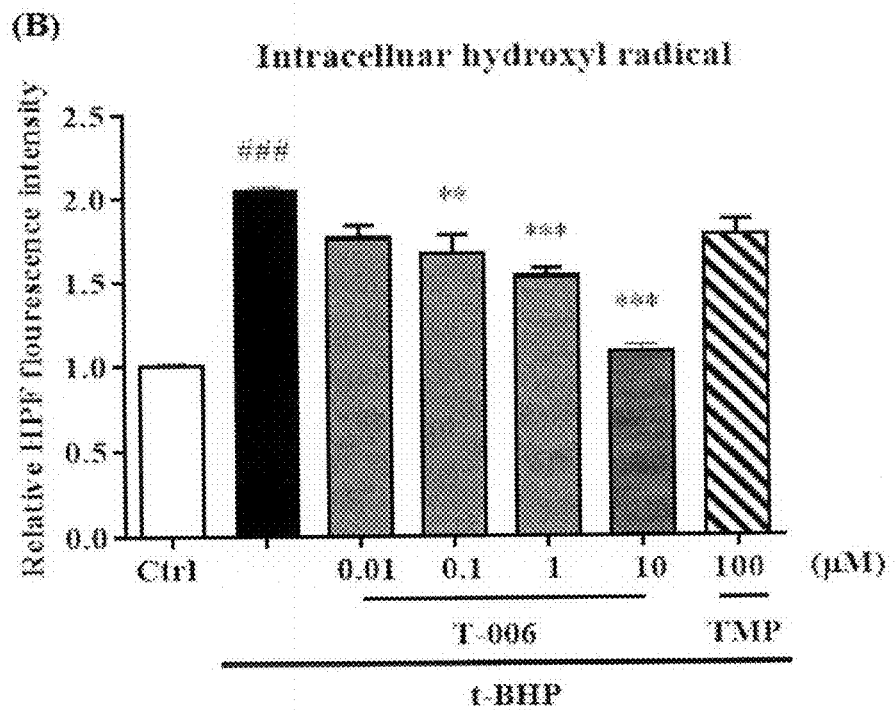
Figure 14C:
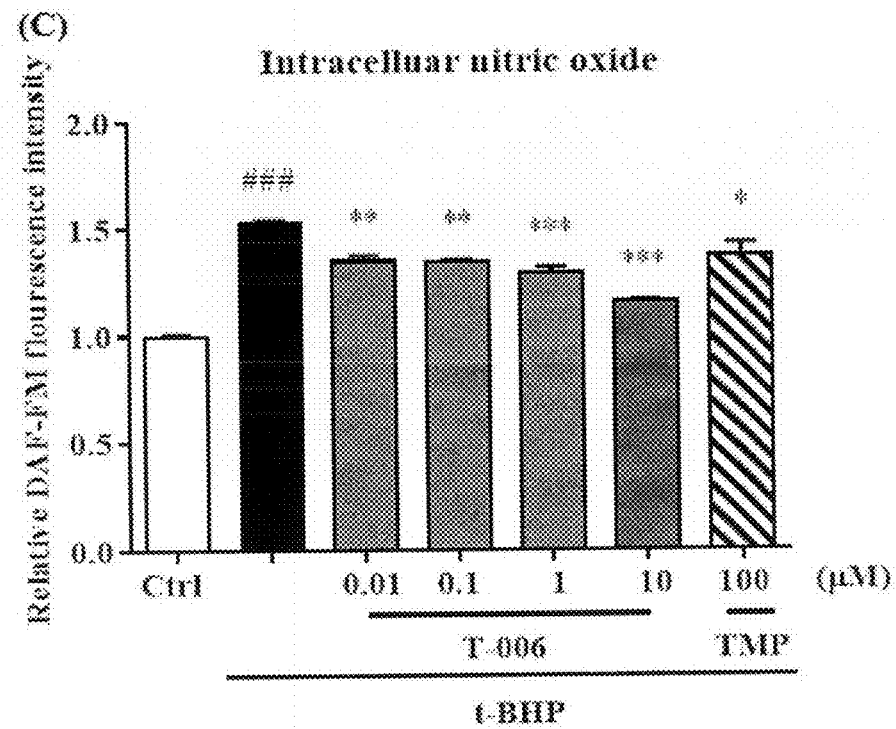
Figure 14D:
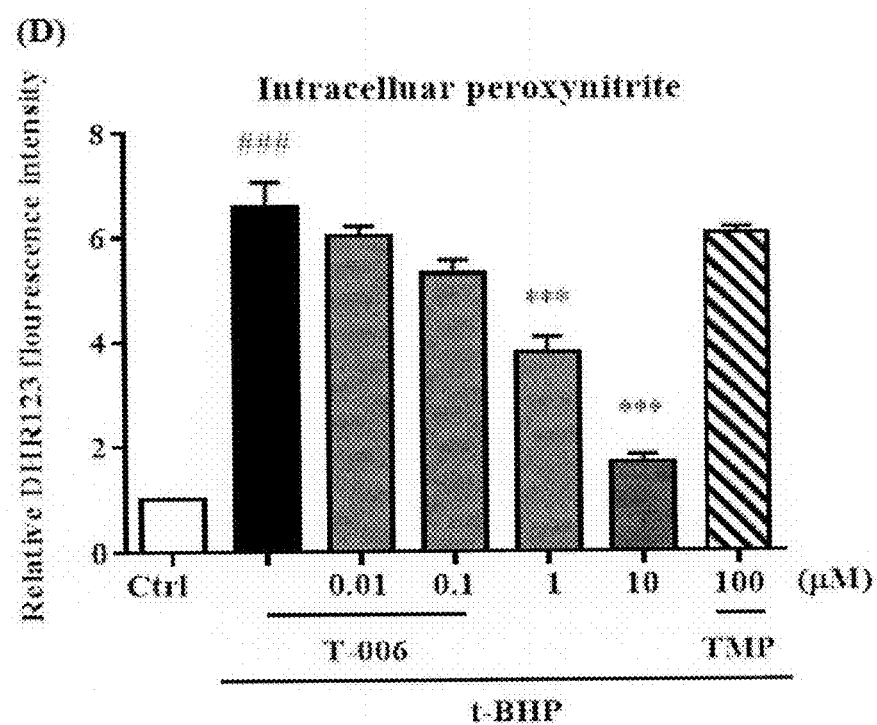

T-006 Reduced t-BHP-induced Apoptosis in PC12 Cells (FIGS. 13A-13C)

PC12 cells were seeded on a 96-well plate and inoculated in a 5% $CO_2$ incubator at 37° C. for 24 hours, and then T-006 and TMP (100 M) in different concentration gradients were added to be pre-incubated for 2 hours. Then the medium was aspirated, and 100 μl t-BHP (100 μM) was added to each well except the wells of the control group, and the cells were cultured in an incubator for 24 hours. Hoechst working fluid was added and the number of PC12 cells was observed and counted under fluorescence microscope. (A) T-006 reduced t-BHP-induced PC12 cell apoptosis. (B) PC12 cell apoptosis statistics. (C) T-006 improved t-BHP-induced mitochondrial membrane potential disorder in PC12 cells. PC12 cells were seeded on a 96-well plate and inoculated in a 5% $CO_2$ incubator at 37° C. for 24 hours, and then T-006 and TMP (100 M) in different concentration gradients were added to be pre-incubated for 2 hours. 2 hours later, 100 μl t-BHP (100 μM) was added to each well except the control group for induction. After completion of the induction, JC-1 working solution was added to each well and mitochondrial membrane potential was monitored and analyzed using flow cytometry. Compared with the control group, ### p<0.001; compared with t-BHP, *p<0.05, p<0.01 and *p<0.001.

EXAMPLE 13

T-006 Reduced the Elevation of ROS and RNS in t-BHP-induced PC12 Cells (FIGS. 14A-14D)

PC12 cells were seeded on 6-well plate and inoculated in a 5% $CO_2$ incubator at 37° C. for 24 hours, and then T-006 and TMP (100 M) in different concentration gradients were added to be pre-incubated for 2 hours. Then the medium was aspirated, and 100 μl t-BHP (100 μM) was added to each well except the wells of the control group, and the cells were cultured in an incubator for 6 hours. Consequently, DCF-DA probes, HFP probes, DAF-FM probes and DHR123 probes were added respectively to determine the total ROS, hydroxyl radicals, nitric oxide radicals and peroxynitrite. (A) DCF-DA probe for determining intracellular total ROS. (B) HFP probe for determining intracellular hydroxyl radicals. (C) DAF-FM probe for determining nitric oxide free radicals. (D) DHR123 probe for determining intracellular peroxynitrite. Compared with the control group, ### p<0.001; compared with t-BHP, *p<0.05, p<0.01 and *p<0.001.

While specific embodiments have been described in detail herein, this is only illustrative of the purpose of the invention and is not intended to limit the scope of the following claims. It should be understood that various substitutions, changes and modifications to the specific embodiments described herein are intended to be within the scope of the invention as defined by the appended claims without departing from the spirit and scope of the invention as defined by the appended claims.

The invention claimed is:

1. A trifluoroacetyl hydrazide compound of the following formula I:

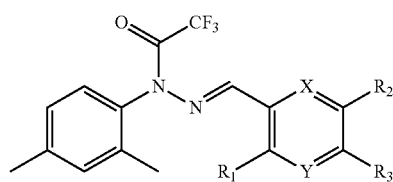

wherein:

$R_1$, $R_2$ and $R_3$ are each independently hydrogen or alkyl group, but cannot be hydrogen at the same time;

X and Y are both N.

2. The compound of claim 1, wherein the alkyl group is a lower alkyl group.

3. The compound of claim 2, wherein $R_1$, $R_2$ and $R_3$ are methyl, and thus the compound has a structure of formula II,

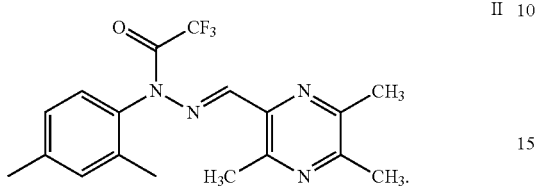

II

4. A method of preparation of the compound of claim 1, the method comprising: 3,5,6-trimethyl-2-pyrazinecarbox-aldehyde is condensed with 2,4-dimethylphenylhydrazide hydrochloride to give an intermediate of phenylhydrazone, which is then reacted with trifluoroacetic anhydride to give final product.

* * * * *